United States Patent
Ross, Jr. et al.

(10) Patent No.: US 9,108,952 B2
(45) Date of Patent: Aug. 18, 2015

(54) PROCESSES TO PRODUCE CERTAIN 2-(PYRIDINE-3-YL)THIAZOLES

(71) Applicant: Dow AgroSciences LLC, Indianapolis, IN (US)

(72) Inventors: Ronald Ross, Jr., Zionsville, IN (US); Carl DeAmicis, Indianapolis, IN (US); Yuanming Zhu, Carmel, IN (US); Noormohamed M. Niyaz, Indianapolis, IN (US); Kim E. Arndt, Carmel, IN (US); Scott P. West, Midland, MI (US); Gary Roth, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/905,220

(22) Filed: May 30, 2013

(65) Prior Publication Data
US 2013/0324737 A1    Dec. 5, 2013

Related U.S. Application Data

(60) Provisional application No. 61/655,086, filed on Jun. 4, 2012.

(51) Int. Cl.
C07D 417/04 (2006.01)
C07D 213/83 (2006.01)

(52) U.S. Cl.
CPC ............ *C07D 417/04* (2013.01); *C07D 213/83* (2013.01)

(58) Field of Classification Search
CPC ....................................................... C07D 417/04
USPC ....................................................... 546/270.4
See application file for complete search history.

(56) References Cited

U.S. PATENT DOCUMENTS 5,219,824 A    6/1993  Sing et al.
2010/0292253 A1  11/2010  Trullinger et al.

FOREIGN PATENT DOCUMENTS

WO    WO2008090382 A1   7/2008
WO    PCT/US2013/043208 A1   11/2013

OTHER PUBLICATIONS

Dorwald, Side Reactions in Organic Synthesis, 2005, Wiley: VCH Weinheim Preface, pp. 1-15 & Chapter 8, pp. 279-308.*
Thompson, et al. Ugi Reactions with Ammonia Offer Rapid Access to a Wide Range of 5-Aminothiazole and Oxazole Derivatives. J. Org. Chem. 74(18): 7084-7093, 2009.

\* cited by examiner

*Primary Examiner* — Patricia L Morris
(74) *Attorney, Agent, or Firm* — Carl D. Corvin

(57) ABSTRACT

The invention disclosed in this document is related to the field of processes to produce certain 2-(pyridine-3-yl)thiazoles as intermediates for the synthesis of pesticidal thiazole amides.

7 Claims, No Drawings

PROCESSES TO PRODUCE CERTAIN 2-(PYRIDINE-3-YL)THIAZOLES

CROSS REFERENCES TO RELATED APPLICATIONS

This application claims priority from, and benefit of, U.S. provisional application 61/655,086 filed on Jun. 4, 2012. The entire content of this provisional application is hereby incorporated by reference into this Application.

FIELD OF THE DISCLOSURE

The invention disclosed in this document is related to the field of processes to produce certain 2-(pyridine-3-yl)thiazoles as intermediates for the synthesis of pesticidal thiazole amides.

BACKGROUND OF THE DISCLOSURE

Controlling pest populations is essential to modern agriculture, food storage, and hygiene. There are more than ten thousand species of pests that cause losses in agriculture. The world-wide agricultural losses amount to billions of U.S. dollars each year. Pests, such as termites, are also known to cause damage to all kinds of private and public structures resulting in billions of U.S. dollars in losses each year. Pests also eat and adulterate stored food, resulting in billions of U.S. dollars in losses each year, as well as deprivation of food needed for people.

Certain pests have or are developing resistance to pesticides in current use. Hundreds of pest species are resistant to one or more pesticides. Accordingly, there exists a continuous need for new pesticides and for processes of forming such pesticides.

WO 2010/129497 (the entire disclosure of which is incorporated herein) discloses certain pesticides. However, the processes of making such pesticides may be both costly and inefficient. Accordingly, there exists a need for processes of efficiently forming such pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"alkynyloxy" means an alkynyl further consisting of a carbon-oxygen single bond, for example, pentynyloxy, hexynyloxy, heptynyloxy, octynyloxy, nonynyloxy, and decynyloxy.

"aryl" means a cyclic, aromatic substituent consisting of hydrogen and carbon, for example, phenyl, naphthyl, and biphenyl.

"cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl.

"cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"cyclohaloalkyl" means a monocyclic or polycyclic, saturated substituent consisting of carbon halo, and hydrogen, for example, 1-chlorocyclopropyl, 1-chlorocyclobutyl, and 1-dichlorocyclopentyl.

"halo" means fluoro, chloro, bromo, and iodo.

"haloalkyl" means an alkyl further consisting of, from one to the maximum possible number of, identical or different, halos, for example, fluoromethyl, difluoromethyl, trifluoromethyl, 1-fluoroethyl, 2-fluoroethyl, 2,2,2-trifluoroethyl, chloromethyl, trichloromethyl, and 1,1,2,2-tetrafluoroethyl.

"heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

DETAILED DESCRIPTION OF THE DISCLOSURE

An embodiment of this invention is illustrated in Scheme One

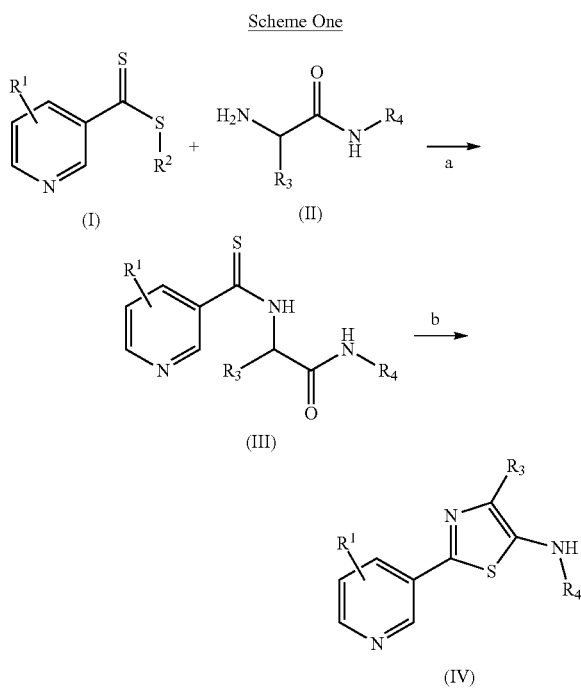

Scheme One wherein
(A) each $R^1$ is independently selected from H, F, Cl, Br, I, CN, NO$_2$, and substituted or unsubstituted $(C_1-C_6)$alkyl, wherein each substituted $R^1$ has one or more substituents independently selected from F, Cl, Br, I, CN, NO$_2$, $(C_1-C_6)$alkyl, and $(C_1-C_6)$haloalkyl;
(B) $R^2$ is selected from substituted or unsubstituted $(C_1-C_6)$alkyl, substituted or unsubstituted $(C_2-C_6)$alkenyl, substituted or unsubstituted $(C_1-C_6)$alkoxy, substituted or unsubstituted $(C_2-C_6)$alkenyloxy, substituted or unsubstituted $(C_3-C_{10})$cycloalkyl, substituted or unsubstituted $(C_3-C_{10})$cycloalkenyl, substituted or unsubstituted $(C_6-C_{20})$aryl, substituted or unsubstituted $(C_1-C_6)$alkyl$(C_6-C_{20})$aryl, and substituted or unsubstituted $(C_1-C_{20})$heterocyclyl, wherein each substituted $R^2$ has one or more substituents independently selected from F, Cl, Br, I, CN, NO$_2$, $(C_1-C_6)$alkyl, $(C_2-C_6)$alkenyl, $(C_1-C_6)$haloalkyl, $(C_2-C_6)$haloalkenyl, $(C_1-C_6)$haloalkyloxy, $(C_2-C_6)$haloalkenyloxy, $(C_3-C_{10})$cycloalkyl, $(C_3-C_{10})$cycloalkenyl, $(C_3-C_{10})$halocycloalkyl, $(C_3-C_{10})$halocycloalkenyl, $(C_6-C_{20})$aryl, and $(C_1-C_{20})$heterocyclyl;
(C) $R^3$ is selected from H, substituted or unsubstituted $(C_1-C_6)$alkyl, substituted or unsubstituted $(C_3-C_{10})$cycloalkyl, substituted or unsubstituted $(C_1-C_6)$alkyl$(C_3-C_{10})$cycloalkyl, substituted or unsubstituted $(C_6-C_{20})$aryl, and substituted or unsubstituted $(C_1-C_6)$alkyl$(C_6-C_{20})$aryl, wherein each substituted $R^3$ has one or more substituents independently selected from F, Cl, Br, and I; and
(D) $R^4$ is selected from H, substituted or unsubstituted $(C_1-C_6)$alkyl, substituted or unsubstituted $(C_3-C_{10})$cycloalkyl, substituted or unsubstituted $(C_1-C_6)$alkyl$(C_3-C_{10})$cycloalkyl, substituted or unsubstituted $(C_6-C_{20})$aryl, substituted or unsubstituted $(C_1-C_6)$alkyl$(C_6-C_{20})$aryl, substituted or unsubstituted $(C_1-C_6)$alkyl$(C_2-C_6)$alkenyl, and substituted or unsubstituted $(C_1-C_6)$alkyl$(C_2-C_6)$alkynyl, wherein each said $R^4$, which is substituted, has one or more substituents selected from F, Cl, Br, I, CN, NO$_2$, $(C_1-C_6)$alkyl, $(C_1-C_6)$haloalkyl, $(C_1-C_6)$alkyloxy, $(C_1-C_6)$haloalkyloxy, $(C_3-C_{10})$cycloalkyl, $(C_3-C_{10})$halocycloalkyl, $(C_6-C_{20})$aryl, and $(C_1-C_{20})$heterocyclyl.

In another embodiment of this invention each $R^1$ is independently selected from H, F, and Cl.

In another embodiment of this invention $R^1$ is H.

In another embodiment of this invention $R^3$ is selected from H, $(C_1-C_6)$alkyl, $(C_1-C_6)$haloalkyl, and $(C_6-C_{20})$aryl.

In another embodiment of this invention $R^3$ is selected from H, CF$_3$, CH$_2$F, CHF$_2$, CH$_3$, CH$_2$CH$_3$, CH(CH$_3$)$_2$, and phenyl.

In another embodiment of this invention $R^3$ is selected from H and CH$_3$.

In another embodiment of this invention $R^4$ is $(C_1-C_6)$alkyl$(C_3-C_{10})$cyclohaloalkyl.

In another embodiment of this invention $R^4$ is selected from H, $(C_1-C_6)$alkyl, $(C_1-C_6)$alkyl$(C_6-C_{20})$aryl, $(C_1-C_6)$haloalkyl, $(C_1-C_6)$alkyl$(C_3-C_{10})$cycloalkyl, $(C_3-C_{10})$cycloalkyl-O—$(C_1-C_6)$alkyl, and $(C_3-C_{10})$cyclohaloalkyl.

In another embodiment of this invention $R^4$ is selected from H, CH$_3$, CH$_2$CH$_3$, CH(CH$_3$)$_2$, CH$_2$CH(CH$_3$)$_2$, cyclopropyl, $(C_6-C_{20})$aryl, CH$_2$-phenyl, CH$_2$-phenyl-OCH$_3$, CH$_2$OCH$_2$-phenyl, CH$_2$CH$_2$CH$_3$, CH$_2$CH$_2$F, CH$_2$CH$_2$OCH$_3$, CH$_2$cyclopropyl, and cyclopropyl-O—CH$_2$CH$_3$.

In another embodiment of this invention $R^4$ is selected from H, CH$_3$, CH$_2$CH$_3$, CH(CH$_3$)$_2$, CH$_2$CH(CH$_3$)$_2$, CH$_2$CH$_2$CH$_3$, cyclopropyl, CH$_2$cyclopropyl, and CH$_2$CH=CH$_2$, CH$_2$C≡CH.

In another embodiment of this invention molecules having a structure according to compound (III) are disclosed as intermediates useful for the synthesis of pesticidal thiazole amides.

In general, S—$R^2$ is a leaving group wherein $R^2$ is part of the leaving group that does not substantially and adversely affect the desired reaction. It is desirable that $R^2$ is a group that beneficially affects the volatility of the thio by-product of the reaction.

In step a, compounds (I) and (II) are reacted to produce compound (III). The reaction can be conducted at room temperature and under ambient pressure, but higher or lower temperatures and pressures can be used, if desired. The reaction is conducted in a polar protic solvent. Examples of such solvents include, but are not limited to, formic acid, n-butanol, isopropanol, n-propanol, ethanol, methanol, acetic acid, and water. Currently, methanol is preferred.

In step b, compound (III) is cyclized using a dehydrating agent. Examples of such dehydrating agents include, but are not limited to, POCl$_3$, H$_2$SO$_4$, SOCl$_2$, P$_2$O$_5$, polyphosphoric acid, p-toluene sulfonic acid, and trifluoroacetic anhydride. The reaction can be conducted at room temperature and under ambient pressure, but higher or lower temperatures and pressures can be used, if desired. Currently, it is preferred if a temperature higher than room temperature is used, preferably, up to and including the boiling point of the solution, for example, a temperature from about 60° C. to about 120° C. can be used. The reaction is conducted in a polar protic solvent. Currently, acetonitrile is preferred.

One advantage of steps a and b over the art is that compound (III) and (IV) are generally produced as substantially pure solids that do not need additional purification procedures. Another advantage with these processes is that in compound (IV)—if R³ is H, it can be halogenated. Consequently, at this point R³ additionally now includes F, Cl, Br, and I (see Scheme Two).

Scheme Two

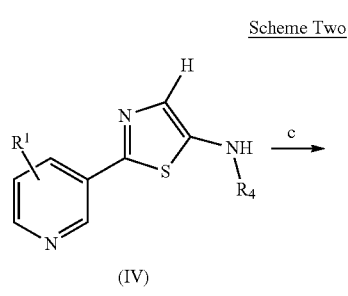

(IV)

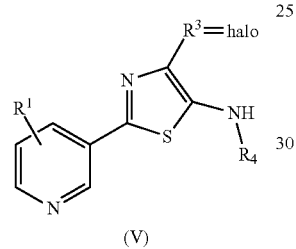

(V)

In step c, any halogenating agent can be used, for example, 1-chloropyrrolidine-2,5-dione, N-bromosuccinimide, and 1-chloromethyl-4-fluoro-1,4-diazoniabicyclo[2.2.2]octane bis(tetrafluoroborate). Polar solvents can be used such as dichloromethane, tetrahydrofuran, ethyl acetate, acetone, dimethylformamide, acetonitrile, and dimethyl sulfoxide. Currently, dichloromethane is preferred. The reaction can be conducted are room temperature and pressure, but higher or lower temperatures and pressures can be used, if desired. Currently, temperatures from about 0° C. to about ambient are preferred.

In another embodiment of this invention R³ is preferably Cl.

Compound (IV) or compound (V) can be further reacted to form certain pesticides disclosed in WO 2010/129497 (the entire disclosure of which is incorporated herein by reference).

EXAMPLES

The examples are for illustration purposes and are not to be construed as limiting the invention disclosed in this document to only the embodiments disclosed in these examples.

Starting materials, reagents and solvents which were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw or ACD Name Pro. If such programs are unable to name a molecule, the molecule is named using conventional naming rules. All NMR are in ppm (δ) and were recorded at 300, 400, or 600 MHz unless otherwise stated.

Example 1

Preparation of N-(4-chloro-2-(pyridin-3-yl)thiazol-5-yl)-N-ethyl-2-methyl-3-(methylthio)propanamide

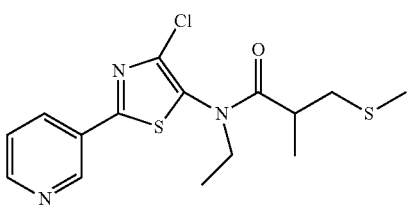 [SMILES: CCN(C(=O)C(C)CSC)c1sc(-c2cccnc2)nc1Cl]

Step 1: Preparation of N-ethyl-2-(pyridin-3-carbothioamido)acetamide

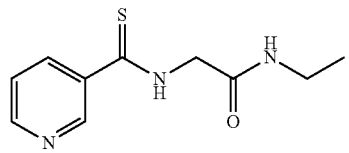

To a dry 3 L round bottom flask equipped with mechanical stirrer, nitrogen inlet, three-stage sequential mercaptan scrubber (bleach, 30% sodium hydroxide, and saturated potassium hydroxide), thermometer, and addition funnel, was charged 2-amino-N-ethylacetamide hydrochloride (SPECS, Catalog #AS-787, 68.8 g, 500 mmol) and methanol (500 mL). The reaction was cooled to 5° C. and triethylamine (50.6 g, 500 mmol) in methanol (50 mL) was added dropwise (note: slightly exothermic to 10° C.). To this mixture was added methyl pyridine-3-carbodithiolate (85.0 g, 500 mmol) in methanol (100 mL) dropwise and the resulting mixture stirred at 5-10° C. for 2 hours. The reaction mixture was allowed to warm to 25° C. and stirred under nitrogen for 2 hours. The reaction mixture was cooled to 5° C. and water (1 L) was added until a solid precipitated from the solution. The solid was collected by vacuum filtration, washed with water (3 L), hexanes (500 mL), and air dried for 16 hours to give N-ethyl-2-(pyridin-3-carbothioamido)acetamide as a yellow fluffy solid (free of any mercaptan odor) which was dried in vacuo at 40° C. for 6 hours. This gave a yellow solid (77.7 g, 70% yield): mp 143-145° C.; $^1$H NMR (400 MHz, CDCl$_3$) δ 9.02 (dd, J=2.4, 0.7 Hz, 1H), 8.86 (s, 1H), 8.70 (dd, J=4.8, 1.6 Hz, 1H), 8.15 (ddd, J=8.0, 2.4, 1.7 Hz, 1H), 7.35 (ddd, J=8.0, 4.8, 0.8 Hz, 1H), 6.05 (s, 1H), 4.43 (d, J=4.5 Hz, 2H), 3.38 (dd, J=13.0, 6.4 Hz, 2H), 1.20 (t, J=7.3 Hz, 3H); $^{13}$C-NMR (101 MHz, CDCl$_3$) δ 195.66, 166.90, 152.00, 147.20, 136.32, 134.96, 123.24, 49.45, 34.92, 14.75; Anal. Calcd. for C$_{10}$H$_{13}$N$_3$OS: C, 53.79; H, 5.87; N, 18.82; S, 14.36. Found: C, 53.77: H, 5.79; N, 18.87; S, 14.52.

Step 2: Preparation of N-ethyl-2-(pyridin-3-yl)thiazol-5-amine

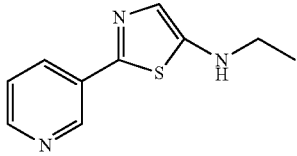

To a dry 1 L round bottom flask equipped with mechanical stirrer, addition funnel and reflux condenser was charged N-ethyl-2-(pyridine-3-carbothioamido)acetamide (50.0 g, 224 mmol) and acetonitrile (400 mL). To this mixture was added phosphorus oxychloride (103 g, 672 mmol) dropwise, and the reaction stirred at ambient temperature for 20 minutes. The reaction mixture was heated to 55° C. and the course of the reaction was monitored by HPLC (YMC AQ column 5% acetonitrile ("ACN") 95% water-0.05% trifluoroacetic acid ("TFA") to 95% ACN 5% water with 0.05% TFA over 20 Min @ 1.0 ml/min). After 2 hours, the reaction was essentially complete. The reaction was cooled to 25° C. and the solvent removed by rotary evaporation to give a thick yellow syrup. The thick yellow syrup was carefully poured into saturated aqueous sodium bicarbonate solution (1.5 L) with rapid stirring. The pH of the resulting yellow solution was adjusted with solid sodium bicarbonate until slightly basic (pH=8), and a yellow solid precipitated from solution. Additional cold water (1 L) was added to the mixture and stirred for an additional 20 minutes. The precipitate was collected by vacuum filtration, and rinsed with water (1 L) and hexanes (500 mL). The collected solid was dried in vacuo at 40° C. for 16 hours to give N-ethyl-2-(pyridin-3-yl)thiazol-5-amine as a yellow solid (36.7 g, 80%): mp 97-98° C.; $^1$H NMR (400 MHz, CDCl$_3$) δ 8.98 (dd, J=2.3, 0.8 Hz, 1H), 8.53 (dd, J=4.8, 1.6 Hz, 1H), 8.07 (ddd, J=8.0, 2.3, 1.6 Hz, 1H), 7.31 (ddd, J=8.0, 4.8, 0.8 Hz, 2H), 6.98 (s, 1H), 3.96 (s, 1H), 3.24 (q, J=5.8 Hz, 2H), 1.31 (t, J=7.2 Hz, 3H); $^{13}$C NMR (101 MHz, CDCl$_3$) δ 152.00, 149.21, 149.21, 146.61, 132.17, 130.44, 123.62, 121.84, 43.09, 14.80. Anal. Calc'd. for C$_{10}$H$_{11}$N$_3$S: C, 58.51; H, 5.40; N, 20.47. Found: C, 58.34: H, 5.40; N, 20.38; ESIMS m/z 205 ([M+H]$^+$).

Step 3: Preparation of 4-chloro-N-ethyl-2-(pyridin-3-yl)thiazol-5-amine hydrochloride

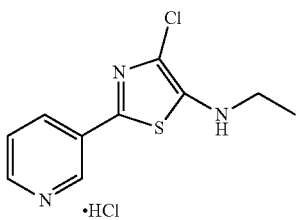

To a dry 500 ml round bottom flask equipped with magnetic stirrer, thermometer, and nitrogen inlet was charged N-ethyl-2-(pyridin-3-yl)thiazol-5-amine (5.1 g, 25 mmol), diethyl ether (200 mL) and dioxane (5 mL). The resulting suspension (not all solid dissolved) was cooled to 5° C., and N-chlorosuccinamide (3.65 g, 27.3 mmol) was added portionwise. After all of the chlorinating agent was added, a brown solid precipitated from solution. The reaction mixture was stirred at 5° C. for 60 minutes, then analyzed by HPLC (YMC AQ column 5% ACN 95% water-0.05% TFA to 95% ACN 5% water with 0.05% TFA over 20 Min @ 1.0 ml/min). HPLC analysis showed no starting material and one major product consistent with the desired chloride. The brown suspension was filtered through a pad of Celite®, and the Celite® pad rinsed with diethyl ether (~20 mL). The filtrate was cooled to 5° C. and acidified with stirring by the addition of 6.5 ml of 4M HCl in dioxane. A yellow solid immediately formed. The solid was collected by vacuum filtration, rinsed with diethyl ether, and dried in vacuo at 40° C. for 2 hours. This gave 4-chloro-N-ethyl-2-(pyridin-3-yl)thiazol-5-amine hydrochloride as a yellow solid (6.3 g, 92%): mp 180-182° C.; $^1$H NMR (400 MHz, DMSO-d$_6$) δ 9.07 (d, J=2.0 Hz, 1H), 8.70 (dd, J=5.4, 1.3 Hz, 1H), 8.59-8.42 (m, 1H), 7.86 (dd, J=8.2, 5.3 Hz, 1H), 5.27 (s, 5H), 3.20 (q, J=7.2 Hz, 2H), 1.23 (t, J=7.1 Hz, 3H); $^{13}$C NMR (101 MHz, DMSO-d$_6$) δ 148.10, 140.19, 138.58, 137.91, 137.01, 132.06, 127.30, 115.89, 43.43, 13.87; Anal. Calcd. for C$_{10}$H$_{11}$Cl$_2$N$_3$S: C, 43.49; H, 4.01; Cl, 25.67; N, 15.21; S, 11.61. Found: C, 43.42: H, 4.01; Cl, 25.55; N, 14.99; S, 11.46.

Step 4: Preparation of N-(4-chloro-2-(pyridin-3-yl)thiazol-5-yl)-N-ethyl-2-methyl-3-(methylthio)propanamide Into a 1 L three-necked flask fitted with a J-KEM type-T temperature probe, overhead stirrer, reflux condenser, and nitrogen inlet was added 4-chloro-N-ethyl-2-(pyridin-3-yl)thiazol-5-amine hydrochloride (75.8 g, 274 mmol) and dichloromethane (500 mL). To the resulting green suspension was added pyridine (55 g, 695 mmol, 2.5 eq) (note: fuming, with exotherm from 20° C. to 26° C.) portionwise over one minute. The reaction turned into a dark green-black solution. To this solution was added N,N-dimethylpyridin-4-amine (DMAP, 16.5 g, 135 mmol, 0.5 eq) (note: no change in reaction appearance or temperature) followed by 2-methyl-3-methylthiopropanoyl chloride (44.3 g, 290 mmol, 1.06 eq), which was added portionwise over one minute. The reaction exothermed from 17° C. to 29° C. during the addition of the acid chloride. The reaction was heated to 35° C. for 19 hours and then cooled to 25° C. for 4 hours. Analysis by HPLC (YMC AQ column 5% acetonitrile ("ACN") 95% water-0.05% trifluoroacetic acid ("TFA") to 95% ACN 5% water with 0.05% TFA over 20 Min @ 1.0 ml/min) showed that the reaction was 95% complete. The black reaction mixture was transferred to a 2 L separatory funnel and dichloromethane (200 mL) and water (300 mL) were added. The phases were separated and the aqueous layer (brown) was extracted with dichloromethane (100 mL) and the dichloromethane extracts combined. The combined dichloromethane extract was washed with brine (300 mL), dried over anhydrous sodium sulfate, filtered, and evaporated (40° C., 40 mmHg, 1 hour). This gave 99.4 g of a black thick oil. The thick black oil was dissolved into dichloromethane (100 mL) and vacuum added to the top of a 240 g solid load cartridge containing 230 g silica gel 60. The solid load cartridge was attached to an ISCO companion XL and the material purified on a 1.5 kg Redisep silica prepacked column using a mobile phase of hexane:ethyl acetate (gradient: 20% ethyl acetate 5 min, 20%-90% ethyl acetate over 70 minutes) with a flow rate of 400 mL/min. The desired compound eluted from the column between 30-50 minutes was collected into 500 mL bottles (fractions 2-16). Fractions 2-9 were pooled (note: fractions 8-9, which were cloudy, were filtered through paper) and rotary evaporated (40° C., 40 mmHg, 2 hours). This gave 56.8 g of a dark yellow oil that was 98% pure by HPLC at 254 nm Fraction 10-15 were filtered and pooled and rotary evaporated (40° C., 40 mmHg, 2 hour) to give a golden oil (27.51 g). The sample was analyzed by HPLC(YMC AQ column 5% ACN 95% water-0.05% TFA to 95% ACN 5% water with 0.05% TFA over 20 Min @ 1.0 ml/min) at 254 nm and showed a purity of 88% and contained 10% thiazoleamine starting material and 2% of a unknown faster moving impurity. The golden oil (27.5 g, 88% pure) was dissolved into ether (50 mL) and a yellow solid precipitated after 1 minute. The mixture was stirred for 15 minutes at 25° C., then hexane (50 mL) was added and the mixture stirred for another 15 minutes at 25° C. The solid was collected by vacuum filtration and the yellow solid washed with ether/hexane (1:1, 25 mL). This gave 19.23 g of N-(4-chloro-2-(pyridin-3-yl)thiazol-5-yl)-N-ethyl-2-methyl-3-(methylthio)propanamide as a yellow solid. Analysis by HPLC showed the purity was 97% at 254 nm. The 56.8 g sample (golden oil, 98% purity) was dissolved into ether (100 mL) and after 1 minute a light tan solid precipitated. The mixture was stirred for 15 minutes at 25° C. and hexane (100 mL) was added. The mixture was stirred for an additional 15 minutes. The solid was collected by vacuum filtration and washed with ether/hexane (1:1, 2×50 mL). This gave 49.67 g light yellow solid. Analysis by HPLC(YMC AQ column 5% ACN 95% water-0.05% TFA to 95% ACN 5% water with 0.05% TFA over 20 Min @ 1.0 ml/min) at 254 nm showed a purity of >99%. The mother liquors from both recrystallization were combined and rotary evaporated (40° C., 40 mmHg, 1 hour). This gave 11.27 g of a dark yellow oil. The oil was re-dissolved into ether (40 mL) and stirred for 30 minutes during which time a dark yellow precipitate formed. Hexane (50 mL) was added and the mixture stirred for 15 minutes. The dark solid was collected by vacuum filtration and washed with ether/hexane (1:1, 2×20 mL). This gave 5.0 g of a brown solid that assayed to >99% pure by HPLC at 254 nm. The recrystallized samples were all combined and mixed manually to give N-(4-chloro-2-(pyridin-3-yl)thiazol-5-yl)-N-ethyl-2-methyl-3-(methylthio)propanamide as a yellow solid (75 g, 85%): mp 80-81° C.; $^1$H NMR (400 MHz, CDCl$_3$) δ 9.12 (d, J=1.9 Hz, 1H), 8.72 (dd, J=4.8, 1.4 Hz, 1H), 8.22 (ddd, J=8.0, 2.2, 1.8 Hz, 1H), 7.43 (ddd, J=8.0, 4.8, 0.6 Hz, 1H), 4.03-3.80 (m, 1H), 3.80-3.59 (m, 1H), 2.97-2.68 (m, 2H), 2.60-2.39 (m, 1H), 2.03 (s, 3H), 1.30-1.16 (m, 6H); $^{13}$C NMR (101 MHz, DMSO-d$_6$) δ 175.66, 162.63, 151.89, 147.14, 138.19, 133.49, 133.23, 128.58, 123.90, 44.81, 38.94, 37.93, 18.16, 16.83, 12.90; Anal. Calcd. for C$_{15}$H$_{18}$ClN$_3$OS$_2$: C, 50.62; H, 5.10; N, 11.81; S, 18.02. Found: C, 50.49: H, 5.21; N, 11.77; S, 17.99.

Example 2

Preparation of N-(4-chloro-2-(pyridin-3-yl)thiazol-5-yl)-N-cyclopropyl-3-(methylthio)propanamide

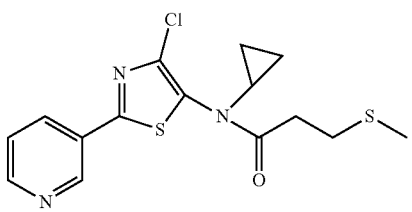 [SMILES: CSCCC(=O)N(c1sc(-c2cccnc2)nc1Cl)C1CC1]

Step 1: Preparation
2-amino-N-cyclopropylacetamide hydrochloride

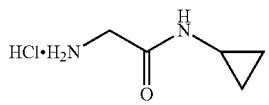

To a solution of 3H-[1,2,3]triazolo[4,5-b]pyridin-3-ol (7.77 g, 57.1 mmol), 2-(tert-butoxycarbonylamino)acetic acid (10 g, 57.1 mmol), cyclopropanamine (3.91 g, 68.5 mmol) and DMAP (8.37 g, 68.5 mmol) in DMF (28 mL) was added N1-((ethylimino)methylene)-N3,N3-dimethylpropane-1,3-diamine hydrogen chloride salt and the mixture stirred at room temperature for 16 h. The mixture was diluted with ethyl acetate, washed with 0.1N aqueous HCl, aqueous NaHCO$_3$ and brine, dried over MgSO$_4$, filtered and concentrated in vacuo to give tert-butyl 2-(cyclopropylamino)-2-oxoethylcarbamate (8.90 g, 41.5 mmol, 72.8%) as a pale yellow oil: $^1$H NMR (400 MHz, CDCl$_3$) δ 6.18 (s, 1H), 3.74 (d, J=5.9 Hz, 2H), 2.71 (m, 1H), 1.45 (s, 9H); 0.84-0.7 (m, 2H), 0.56-0.43 (m, 2H); EIMS m/z 214 ([M]$^+$). To a solution of tert-butyl 2-(cyclopropylamino)-2-oxoethylcarbamate (8.5 g, 39.7 mmol) in dioxane (20 mL) was added HCl (100 mmol, 25 mL 4 M in dioxane) and the mixture stirred at 10° C. for 3 h. The mixture was diluted with hexanes and filtered under vacuum to give 2-amino-N-cyclopropylacetamide, HCl salt as a white solid (5.2 g, 83%): mp 139-142° C.; $^1$H NMR (400 MHz, DMSO-d$_6$) δ 8.66 (bs, 1H), 8.19 (bs, 3H), 3.46 (s, 2H), 2.73-2.60 (m, 1H), 0.71-0.60 (m, 2H), 0.48-0.36 (m, 2H).

Step 2: Preparation of N-cyclopropyl-2-(pyridine-3-carbothioamido)acetamide

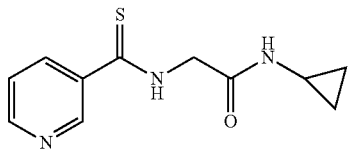 [SMILES: O=C(CNC(=S)c1cccnc1)NC1CC1]

To a solution of methylpyridine-3-carbodithioate (2.97 g, 17.52 mmol) in methanol (10 mL) was added a solution of 2-amino-N-cyclopropylacetamide (2 g, 17.52 mmol) (HCl salt) and triethylamine (3.55 g, 35.0 mmol). The mixture was stirred at room temperature for 1 hour and then diluted with ethyl acetate and washed with saturated aqueous NaHCO$_3$, brine, dried over MgSO$_4$, filtered, and concentrated in vacuo to give N-cyclopropyl-2-(pyridine-3-carbothioamido)acetamide as a yellow solid (3.60 g, 83%): mp 152-153° C.; $^1$H NMR (400 MHz, DMSO-d$_6$) δ 10.60 (s, 1H), 8.91 (ddd, J=7.0, 2.3, 0.7 Hz, 1H), 8.76-8.56 (m, 1H), 8.10 (m, 2H), 7.57-7.32 (m, 1H), 4.26 (m, 2H), 2.73-2.57 (m, 1H), 0.77-0.61 (m, 2H), 0.50-0.29 (m, 2H); ESIMS (m/z) 234 ([M−H]$^-$).

Step 3: Preparation of N-cyclopropyl-2-(pyridin-3-yl)thiazol-5-amine

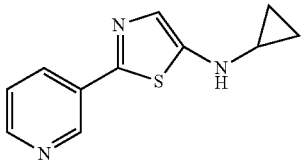 [SMILES: c1cncc(-c2ncc(NC3CC3)s2)c1]

N-Cyclopropyl-2-(pyridine-3-carbothioamido)acetamide (1.00 g, 4.25 mmol) was dissolved in acetonitrile (5 mL) in a dry flask and phosphoryloxy trichloride (3.26 g, 21.25 mmol) was added, dropwise. The mixture was warmed to 100° C. and stirred for 1 hour. The mixture was cooled to room temperature and the yellow solid filtered under vacuum. This solid was washed with acetonitrile and dried under vacuum to give 0.36 g of N-cyclopropyl-2-(pyridin-3-yl)thiazol-5-amine HCl salt (LCMS and $^1$H-NMR indicated 100% purity). The filtrate was diluted with ethyl acetate and carefully basified with saturated aqueous NaHCO$_3$. The organic phase was separated and washed with brine, dried over MgSO$_4$, and concentrated in vacuo to give N-cyclopropyl-2-(pyridin-3-yl)thiazol-5-amine as a brown oil (0.45 g, 3.47 mmol, 82%): $^1$H NMR (400 MHz, CDCl$_3$) δ 9.10 (d, J=2.1 Hz, 1H), 8.68 (dd, J=5.5, 1.2 Hz, 1H), 8.63-8.58 (m, 1H), 7.89 (dd, J=8.1, 5.4 Hz, 1H), 7.07 (d, J=7.8 Hz, 1H), 2.57 (dt, J=10.0, 3.3 Hz, 1H), 0.85-0.68 (m, 2H), 0.57-0.45 (m, 2H); ESIMS (m/z) 216 ([M−H]$^−$).

Step 4: Preparation of 4-chloro-N-cyclopropyl-2-(pyridin-3-yl)thiazol-5-amine

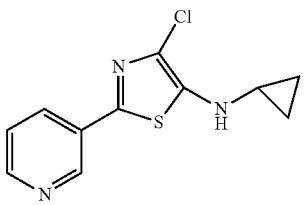 [SMILES: Clc1nc(-c2cccnc2)sc1NC1CC1]

To a solution of N-cyclopropyl-2-(pyridin-3-yl)thiazol-5-amine (1.00 g, 4.60 mmol) in acetonitrile (2 mL) was added 1-chloropyrrolidine-2,5-dione (645 mg, 4.83 mmol) and the mixture stirred at 0° C. for 1 h. The mixture was filtered and the filtrate was treated with excess HCl (4M in dioxane) to give 4-chloro-N-cyclopropyl-2-(pyridin-3-yl)thiazol-5-amine as a brown solid: mp 56-60° C.

Step 5: Preparation of N-(4-chloro-2-(pyridin-3-yl)thiazol-5-yl)-N-cyclopropyl-3-(methylthio)propanamide To a solution of 4-chloro-N-cyclopropyl-2-(pyridin-3-yl)thiazol-5-amine HCl salt (288 mg, 1 mmol) and DMAP (305 mg, 2.500 mmol) in CH$_2$ClCH$_2$Cl (1 mL) was added 3-(methylthio)propanoyl chloride (166 mg, 1.200 mmol), and the mixture stirred at room temperature for 1 h. The mixture was diluted with ethyl acetate, mixed with aqueous NaHCO$_3$ (10 mL). The organic phase was separated, rinsed with brine (2×), dried over MgSO$_4$ and concentrated in vacuo to give a yellow gum. This gum was purified on reverse phase column chromatography (C-18, CH$_3$CN/H$_2$O) to give N-(4-chloro-2-(pyridin-3-yl)thiazol-5-yl)-N-cyclopropyl-3-(methylthio)propanamide (82 mg, 22%) as a brown gum: $^1$H NMR (400 MHz, CDCl$_3$) δ 9.10 (s, 0.6H), 9.02 (s, 0.4H), 8.71 (s, 6H), 8.61 (d, J=3.4 Hz, 0.4H), 8.21 (d, J=7.6 Hz, 1H), 8.19-8.10 (m, 1H), 7.41 (d, J=5.6, 0.6H), 7.35 (dd, J=8.3, 4.5 Hz, 0.4H), 3.16 (bs, 1H), 2.91 (s, 3H), 2.88-2.72 (m, 2H), 2.11 (m, 2H), 0.85 (m, 4H); ESIMS (m/z) 354.56 ([M+H]$^+$).

Example 3

Preparation of N-(4-chloro-2-(pyridin-3-yl)thiazol-5-yl)-N,2-dimethyl-3-(methylthio)propanamide

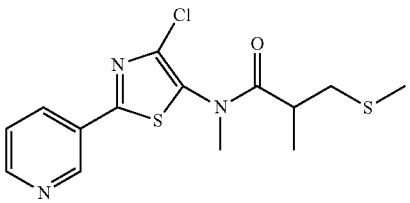 [SMILES: CSCC(C)C(=O)N(C)c1sc(-c2cccnc2)nc1Cl]

Step 1: Preparation of N-methyl-2-(pyridine-3-carbothioamido)acetamide

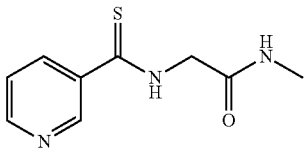

A 5 liter three-necked round bottom flask was fitted with a nitrogen inlet over a dropping funnel, a mechanical stirrer, and a reflux condenser. A tube from the top of the condenser was plumbed through a 1 liter bump flask and then into a sparge tube in another 5 liter three-neck stirred flask filled with 2.5 liter of 12% pool bleach. The outlet of the bleach flask was plumbed through an alligator trap with about 250 mL of 12% bleach solution. The reactor was charged with 2-amino-N-methylacetamide (160 g, 1.81 mol) and acetonitrile (3 L) to give a cloudy solution. The dropping funnel was charged with methylpyridine-3-carbodithioate (307 g, 1.81 mol) and acetonitrile (200 mL). The addition of the dithioate took about 20 min and the reaction was swept with a good stream of nitrogen. A slight exotherm was noted upon the addition (about 3° C.). After the addition was complete, the dropping funnel was rinsed with 550 mL of acetonitrile to bring the total volume of acetonitrile to 3750 mL. After stirring for about 10 min, the red solution precipitated to give a cottage cheese-like solid which would not stir. The dropping funnel was replaced with a ¼ inch straight tube to bubble nitrogen into the reactor. The reactor was heated slowly to about 45-50° C. to form a reddish solution and then allowed

13 to cool back down slowly to room temperature and crystallize to a fine yellowish needle-like solid which stirred easily. The needles were collected by vacuum filtration and washed with 100 mL of acetonitrile. The solid was dried under vacuum at 40° C. for 16 h to give N-methyl-2-(pyridine-3-carbothioamido)acetamide (268.6 g, 71%) as a light yellow solid: mp 135-137° C.; $^1$H NMR (400 MHz, DMSO-$d_6$) δ 10.65 (s, 1H), 8.95 (dd, J=2.4, 0.7 Hz, 1H), 8.67 (dd, J=4.8, 1.6 Hz, 1H), 8.14 (ddd, J=8.0, 2.3, 1.7 Hz, 1H), 7.95 (d, J=4.3 Hz, 1H), 7.48 (ddd, J=7.9, 4.8, 0.7 Hz, 1H), 4.34 (s, 2H), 2.62 (d, J=4.6 Hz, 3H); $^{13}$C NMR (101 MHz, DMSO-$d_6$) δ 194.98, 165.77, 150.37, 146.40, 135.25, 134.04, 121.51, 47.66, 24.41; Anal. Calcd. for $C_9H_{11}N_3OS$: C, 51.65; H, 5.30; N, 20.08; S, 15.32. Found: C, 51.47: H, 5.30; N, 20.01; S, 15.53.

Step 2: Preparation of N-methyl-2-(pyridin-3-yl)thiazol-5-amine

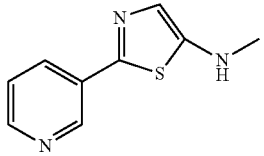

To a dry 2 L round bottom flask equipped with mechanical stirrer, addition funnel and reflux condenser was charged N-methyl-2-(pyridine-3-carbothioamido)acetamide (100 g, 478 mmol) and acetonitrile (1 L). To this mixture was added phosphorus oxychloride (256 g, 1672 mmol) portionwise over 10 minutes. The reaction mixture was stirred at ambient temperature for 10 minutes during which time a slight exotherm occurred from 22° C. to 34° C. (Note: some solid remained undissolved in the reaction mixture, and the mixture became thick, but still stirred reasonably well). The reaction mixture was heated to 85° C. (refluxing gently). After 3 hours, all of the solid had dissolved, forming a dark amber solution. Analysis of an aliquot by TLC (70% ethyl acetate: 30% hexanes) after 4 hours indicated that the reaction was essentially complete. The reaction mixture was allowed to cool to 25° C. and the solvent removed by rotary evaporation. The residue was dissolved in water and treated with solid sodium bicarbonate until slightly basic (pH ~8) with continuous stirring (Note: No attempt was made to control the temperature, and the flask was slightly warm to the touch). A brown precipitate started to form after a few minutes. The mixture was continued to stir at 25° C. for 16 hours. The brown solid was collected by vacuum filtration and washed with water. This gave a tan solid wet cake (91 g) which was then dried in vacuo at 40° C. to a constant weight. This gave N-methyl-2-(pyridin-3-yl)thiazol-5-amine as a sand colored solid (68.5 g, 75%): mp 140-141° C.; $^1$H NMR (400 MHz, CDCl$_3$) δ 8.98 (dd, J=2.3, 0.7 Hz, 1H), 8.53 (dd, J=4.8, 1.6 Hz, 1H), 8.07 (ddd, J=8.0, 2.2, 1.7 Hz, 1H), 7.40-7.21 (m, 1H), 6.96 (s, 1H), 4.18 (s, 1H), 2.96 (s, 3H); $^{13}$C NMR (101 MHz, Chloroform) δ 153.23, 149.15, 146.54, 132.23, 130.47, 123.65, 121.20, 34.48; Anal. Calc'd. for $C_9H_9N_3S$: C, 56.52; H, 4.74; N, 21.97; S, 16.77. Found: C, 56.31: H, 4.74; N, 21.81; S, 16.96.

14

Step 3: Preparation of 4-chloro-N-methyl-2-(pyridin-3-yl)thiazol-5-amine

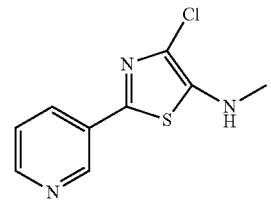

To a dry 100 ml round bottom flask equipped with magnetic stirrer, thermometer, and nitrogen inlet was charged N-methyl-2-(pyridin-3-yl)thiazol-5-amine (0.528 g, 2.76 mmol) and dichloromethane (50 mL). The resulting solution was cooled to 5° C., followed by the portionwise addition of the solid N-chlorosuccinamide. After all of the chlorinating agent was added a dark brown solution formed. The solution was stirred at 5° C. for 20 minutes, then analyzed an aliquot by HPLC(YMC AQ column 5% ACN 95% water-0.05% TFA to 95% ACN 5% water with 0.05% TFA over 20 Min @ 1.0 ml/min) HPLC analysis showed no starting material and one major product. The reaction mixture was poured into a separatory funnel containing dichloromethane (50 mL) and washed with water (2×10 mL) followed by saturated aqueous sodium chloride solution (10 mL). The organic phase was dried over anhydrous magnesium sulfate, filtered, and rotary evaporated to give a powdery brown solid (0.51 g). The solid was purified on an ISCO Combiflash Rf (silica gel 80 g cartridge, mobile phase A=hexane, B=ethyl acetate, gradient 0% B to 100% B over 20 minutes). Fractions were collected into 25 mL test tubes. The tubes containing the desired material were combined and rotary evaporated to afford 4-chloro-N-methyl-2-(pyridin-3-yl)thiazol-5-amine as a canary yellow solid (0.32 g, 51%); $^1$H NMR (400 MHz, CDCl$_3$) δ 8.97 (dd, J=2.3, 0.7 Hz, 1H), 8.54 (dd, J=4.8, 1.6 Hz, 1H), 8.07 (ddd, J=8.0, 2.3, 1.6 Hz, 1H), 7.45-7.14 (m, 1H), 4.07 (dd, J=40.5, 38.0 Hz, 1H), 3.03 (d, J=5.3 Hz, 3H); $^{13}$C NMR (101 MHz, CDCl$_3$) δ 149.55, 146.03, 145.60, 145.28, 131.73, 129.71, 123.64, 117.37, 35.75; Anal. Calc'd. for $C_9H_8ClN_3S$: C, 49.89; H, 3.57; N, 18.62; S, 14.21. Found: C, 48.03: H, 3.64; N, 18.42; S, 14.23.

Step 4: Preparation of N-(4-chloro-2-(pyridin-3-yl)thiazol-5-yl)-N,2-dimethyl-3-(methylthio)propanamide To a dry 500 ml round bottom flask equipped with magnetic stirrer, thermometer, and nitrogen inlet was added 4-chloro-N-methyl-2-(pyridin-3-yl)thiazol-5-amine (22 g, 97 mmol) and dichloromethane (250 mL). The suspension was stirred at room temperature while pyridine (8.48 g, 107 mmol) and DMAP (1.20 g, 9.75 mmol) were added. To this suspension was added 2-methyl-3-(methylthio)propanoyl chloride (17.8 g, 117 mmol) over 5 minutes. During the addition all solids went into solution and the reaction was exothermic from 20° C. to 30° C. The reaction was stirred at ambient temperature for 16 h. The mixture was checked by HPLC(YMC AQ column 5% ACN 95% water-0.05% TFA to 95% ACN 5% water with 0.05% TFA over 20 Min @ 1.0 ml/min) which showed complete conversion of all starting material. The reaction mixture was diluted with dichloromethane and water was then added. The mixture was poured into a separatory funnel with dichloromethane and water and the layers separated. The organic phase was washed with brine, dried over anhydrous magnesium sulfate, filtered, and rotary evaporated to afford 33.6 g of a dark oil. The oil was purified on an ISCO Combiflash Rf (330 g silica gel cartridge, mobile phase A=hexane, B=ethyl acetate, gradient 0% B to 100% B over 20 minutes). The fractions were collected into 25 mL test tubes. The tubes containing the desired product were combined and the solvent removed by rotary evaporation. This afforded 22.8 g of a thick yellow liquid in 68.4% isolated yield. The entire sample crystallized and hexane (200 mL) was added to give a slurry. The slurry was vacuum filtered and the solid allowed to air dry. This gave N-(4-chloro-2-(pyridin-3-yl)thiazol-5-yl)-N,2-dimethyl-3-(methylthio)propanamide as an off-white solid; mp 75-80° C.; $^1$H NMR (400 MHz, CDCl$_3$) δ 9.12 (d, J=1.4 Hz, 1H), 8.73 (d, J=3.8 Hz, 1H), 8.34-8.09 (m, 1H), 7.43 (dd, J=7.9, 4.9 Hz, 1H), 3.30 (s, 3H), 3.06-2.70 (m, 2H), 2.49 (d, J=7.4 Hz, 1H), 2.04 (s, 3H), 1.21 (d, J=6.4 Hz, 3H); $^{13}$C NMR (101 MHz, DMSO-d$_6$) δ 175.22, 162.37, 151.91, 146.53, 136.46, 134.64, 133.35, 127.98, 124.27, 37.47, 36.71, 36.47, 17.56, 15.44; Anal. Calcd. for C$_{14}$H$_{16}$ClN$_3$OS$_2$: C, 49.18; H, 4.72; N, 12.29; S, 18.76. Found: C, 49.04: H, 4.68; N, 12.29; S, 18.68.

What is claimed is:

1. A process comprising

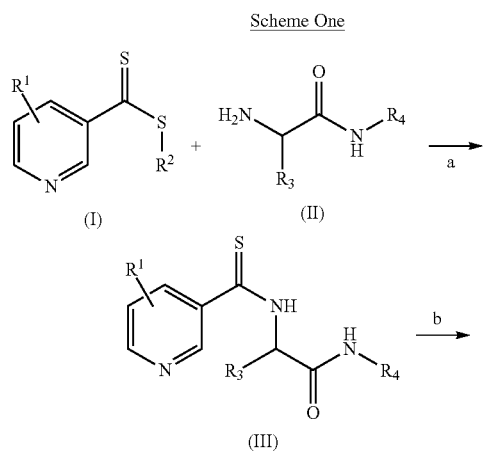

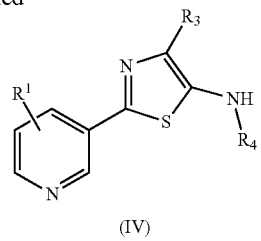

wherein
(i) reacting compound (I) with compound (II) in step a to produce compound (III), wherein said reacting is conducted in a polar protic solvent under ambient pressure; followed by
(ii) cyclizing compound (III) using a dehydrating agent to produce compound (IV) wherein said dehydrating agent is selected from the group consisting of POCl$_3$, H$_2$SO$_4$, SOCl$_2$, P$_2$O$_5$, polyphosphoric acid, p-toluene sulfonic acid, trifluoroacetic anhydride, or a mixture thereof, and wherein said cyclizing is conducted at ambient pressure, and temperatures from 60° C. to 120° C.;
wherein
(A) R$^1$ is H;
(B) R$^2$ is a (C$_1$-C$_6$)alkyl;
(C) R$^3$ is H or (C$_1$-C$_6$)alkyl; and
(D) R$^4$ is H, (C$_1$-C$_6$)alkyl, or cyclopropyl.

2. A process according to claim 1 wherein said polar protic solvent is formic acid, n-butanol, isopropanol, n-propanol, ethanol, methanol, acetic acid, water, or a mixture thereof.

3. A process according to claim 1 wherein said polar protic solvent is methanol.

4. A process according to claim 1 further comprising halogenating said R$^3$ of compound (IV) to F, Cl, Br, or I, in a polar solvent, at a temperature from 0° C. to ambient.

5. A process according to claim 4 wherein said halogenating is conducted in a polar solvent selected from dichloromethane, tetrahydrofuran, ethyl acetate, acetone, dimethylformamide, acetonitrile, and dimethyl sulfoxide.

6. A process according to claim 5 wherein said polar solvent is dichloromethane.

7. A process according to any one of claims 4, 5, and 6, wherein R$^3$ is Cl.

* * * * *